United States Patent
Nasedkin et al.

(10) Patent No.: US 10,470,703 B2
(45) Date of Patent: Nov. 12, 2019

(54) SYSTEM AND METHOD FOR FUNCTIONAL STATE AND/OR PERFORMANCE ASSESSMENT AND TRAINING PROGRAM ADJUSTMENT

(71) Applicants: Valeriy Nasedkin, Kauniainen (FI); Leonid Vasilyevich Masakov, Espoo (FI)

(72) Inventors: Valeriy Nasedkin, Kauniainen (FI); Leonid Vasilyevich Masakov, Espoo (FI)

(*) Notice: Subject to any disclaimer, the term of this patent is extended or adjusted under 35 U.S.C. 154(b) by 381 days.

(21) Appl. No.: 14/918,644

(22) Filed: Oct. 21, 2015

(65) Prior Publication Data

US 2016/0143578 A1    May 26, 2016

Related U.S. Application Data

(63) Continuation of application No. 13/912,178, filed on Jun. 6, 2013, now abandoned.

(51) Int. Cl.

| | |
|---|---|
| A61B 5/00 | (2006.01) |
| A61B 5/0205 | (2006.01) |
| A61B 5/0402 | (2006.01) |
| A61B 5/0476 | (2006.01) |
| A61B 5/0488 | (2006.01) |
| A61B 5/11 | (2006.01) |
| G06F 19/00 | (2018.01) |
| A61B 5/04 | (2006.01) |
| A61B 5/024 | (2006.01) |

(52) U.S. Cl.
CPC ............ *A61B 5/486* (2013.01); *A61B 5/0022* (2013.01); *A61B 5/0205* (2013.01); *A61B 5/0402* (2013.01); *A61B 5/04012* (2013.01); *A61B 5/0476* (2013.01); *A61B 5/0488* (2013.01); *A61B 5/1118* (2013.01); *A61B 5/4035* (2013.01); *A61B 5/4866* (2013.01); *A61B 5/7282* (2013.01); *A61B 5/7425* (2013.01); *G06F 19/3481* (2013.01); *A61B 5/02405* (2013.01)

(58) Field of Classification Search
None
See application file for complete search history.

(56) References Cited

U.S. PATENT DOCUMENTS

| | | | |
|---|---|---|---|
| 6,487,442 B1 * | 11/2002 | Wood ................... | A61B 5/0468 600/515 |
| 7,367,950 B1 * | 5/2008 | Masakov ................ | A61B 5/00 128/920 |
| 8,033,959 B2 * | 10/2011 | Oleson ............... | A63B 24/0062 482/9 |

(Continued)

*Primary Examiner* — Carl H Layno
*Assistant Examiner* — Manolis Pahakis
(74) *Attorney, Agent, or Firm* — Steven J. Sullivan

(57) ABSTRACT

A system and method for training program generation and modification based on user input goal data and assessed functional state and/or workload performance. A user-interface preferably operating on a mobile device permits a user to record bio-signals indicative of functional state. Assessments are performed on the received bio-signal data to produce training session targets based on the current functional state of the user. Workload performance may be monitored and the training session targets modified based on measured past performance to improve future performance. Various embodiments are disclosed.

12 Claims, 2 Drawing Sheets

(56) References Cited

U.S. PATENT DOCUMENTS

| | | | |
|---|---|---|---|
| 9,864,843 B2* | 1/2018 | Wisbey | G16H 20/10 |
| 2002/0045835 A1* | 4/2002 | Masakov | A61B 5/0205 |
| | | | 600/481 |
| 2003/0013995 A1* | 1/2003 | Oshima | A61B 5/0245 |
| | | | 600/587 |
| 2005/0124906 A1* | 6/2005 | Childre | A61B 5/02405 |
| | | | 600/529 |
| 2005/0256414 A1* | 11/2005 | Kettunen | A61B 5/024 |
| | | | 600/509 |
| 2006/0032315 A1* | 2/2006 | Saalastic | A61B 5/222 |
| | | | 73/808 |
| 2006/0047202 A1* | 3/2006 | Elliott | A61B 5/0205 |
| | | | 600/485 |
| 2006/0063980 A1* | 3/2006 | Hwang | A61B 5/222 |
| | | | 600/300 |
| 2009/0069156 A1* | 3/2009 | Kurunmaki | A63B 24/0062 |
| | | | 482/9 |
| 2010/0174205 A1* | 7/2010 | Wegerif | A61B 5/02405 |
| | | | 600/515 |
| 2010/0298899 A1* | 11/2010 | Donnelly | A61B 5/02055 |
| | | | 607/6 |
| 2011/0004110 A1* | 1/2011 | Shusterman | G16H 50/20 |
| | | | 600/509 |
| 2011/0105859 A1* | 5/2011 | Popovic | A61B 5/0205 |
| | | | 600/301 |
| 2012/0010478 A1* | 1/2012 | Kinnunen | A61B 5/02405 |
| | | | 600/301 |
| 2013/0158423 A1* | 6/2013 | Kapoor | A61B 5/0432 |
| | | | 600/523 |
| 2013/0178335 A1* | 7/2013 | Lin | A63B 71/06 |
| | | | 482/8 |
| 2014/0073486 A1* | 3/2014 | Ahmed | A61B 5/02405 |
| | | | 482/9 |
| 2014/0364702 A1* | 12/2014 | Nasedkin | A61B 5/0022 |
| | | | 600/301 |
| 2015/0251074 A1* | 9/2015 | Ahmed | A61B 5/02405 |
| | | | 700/91 |

* cited by examiner

SYSTEM AND METHOD FOR FUNCTIONAL STATE AND/OR PERFORMANCE ASSESSMENT AND TRAINING PROGRAM ADJUSTMENT

CROSS REFERENCE TO RELATED APPLICATIONS

This application is a continuation of U.S. patent application Ser. No. 13/912,178, entitled Apparatus and Method for Functional State and/or Performance Assessment and Training Program Adjustment, filed on Jun. 6, 2013, and having an inventor named above. Application Ser. No. 13/912,178 is related to U.S. patent application Ser. No. 13/912,176, entitled Apparatus And Method For Assessing Functional State Of Body Systems Including Electromyography by Masakov, and filed on Jun. 6, 2013, which is hereby incorporated by reference as though disclosed herein. The present application is also related to U.S. Pat. No. 6,572,558 issued to Masakov, et al., for an Apparatus and Method for Non-Invasive Measurement of Current Functional State and Adaptive Response in Humans which is hereby incorporated by reference as though disclosed herein.

FIELD OF THE INVENTION

The present invention relates to physical exercise training programs and, more specifically, to assessment of the current functional state of a person and/or the workload performed by the user and adjustment of a training program for that user based on assessment results.

BACKGROUND OF THE INVENTION

Various physical exercise training program models and devices are known in the art. They may be divided into five groups:

1. Solutions that present a training program or schedule based on historically collected empirical data. These programs may be generic or specific and may cover a time period of a week to a year. For example, marathon training typically includes a 6-month training program with miles increasing each week and tapering towards the end.
2. Solutions that assess the magnitude of the training load such as speed, distance, elapsed time, amount of weight lifted, etc.
3. Solutions that monitor changes in heart rate and warn the user via an audio signal when his or her pulse moves above or below a predetermined heart rate zone.
4. Solutions that assess the functional state of a person and provide information of the individual's current physiological state and may also provide an indication of heart rate zones for various levels of training loads.
5. Solutions that are a combination of Solutions 3 and 4.

While beneficial in advancing the field, the prior art is disadvantageous in that it is not responsive to the individual needs or current physiological state of the specific person undergoing training. Generic programs may be inappropriate or not sufficiently accurate for a given individual. Furthermore, daily changes in the functional state of a person may make the dictates of a generic program inapplicable on a given day/period. If an athlete continues with the proscribed training regime when his/her functional state does not support it, then the athlete risks injury and/or a substantial setback in their training.

In addition, if an attempt is made to more closely analyze the training program and/or physiological assess the person using currently available technology, several disadvantages arise. These include, but are not limited to, a significant amount of time is/may be required, multiple assessments are needed, and exercise is interrupted during assessment, among other disadvantages.

Thus, a need exists to expediently and/or contemporaneously capture the data indicative of the functional state of a subject under test (SUT), to assess this data to determine current functional state, and to adjust a training program in response thereto to improve the training process and therefore deliver better physical performance to the user. A need further exists to achieve the above in a manner that is convenient, lightweight, easy-to-use and effective.

Prior art systems are further disadvantageous in that they do not assess the work performed nor adjust the training program as needed based on the workload assessment.

SUMMARY OF THE INVENTION

Accordingly, it is an object of the present invention to provide an assessment and training program adjustment system that addresses the shortcomings of the prior art.

It is another object of the present invention to provide such a system that assess the functional state of a user and modifies a prospective training program based on the functional state assessment.

It is also an object of the present invention to provide such a system that measures the workload performed by the user and modifies a prospective training program for improved performance.

These and related objects of the present invention are achieved by use of a system and method for functional state and/or performance assessment and training program adjustment as described herein.

The attainment of the foregoing and related advantages and features of the invention should be more readily apparent to those skilled in the art, after review of the following more detailed description of the invention taken together with the drawings.

DETAILED DESCRIPTION

Figure 1:
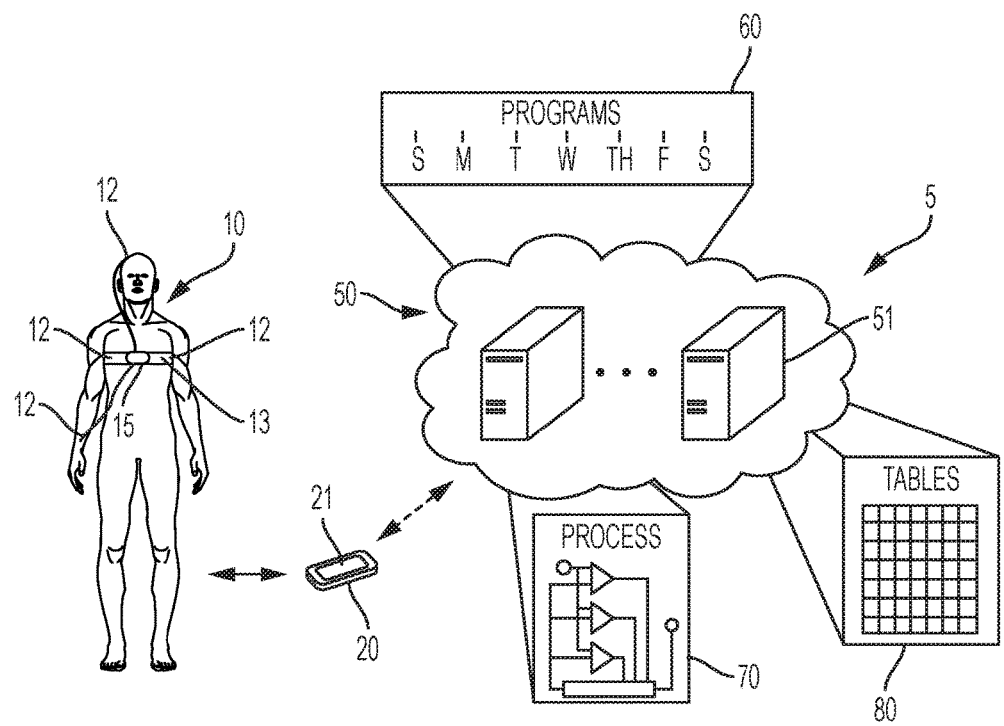
FIG. 1 is a diagram of one embodiment of a physical state assessment and training program adjustment system in accordance with the present invention.

Referring to FIG. 1, a diagram of one embodiment of a physical state assessment and training program adjustment system 5 in accordance with the present invention is shown. System 5 preferably operates in concert with the mobile device platform or environment, to afford the convenience and mobility of that platform. In addition, mobile device communication permits real-time assessment of the workload performed by the user. The user-interface that operates on the mobile device to carry out the present invention may evolve as mobile communication evolves without departing from the present invention.

System 5 may include a sensor and transmitter unit (SATU) 10, a user-interface 21 that executes on mobile device (MD) 20 and processing unit (PU) 50 that may execute on a cloud-based computer (or other processor) 51. Further, the user-interface may be invoked as an application executing on the mobile device, termed, for example, Adaptive Training application. Depending on the magnitude of the processing load and the power of the mobile device, processing may take place on the cloud and/or the mobile. It is anticipated that initially more robust processing will occur on the cloud computer, yet as mobile device technology improves, some or all of the assessment/adjustment processing may move to the mobile device, particularly for less robust assessments/adjustments.

For pedagogical purposes, the system of FIG. 1 will be described with the assessment and training program adjustment operating primarily on the cloud computer(s) 51, though it is to be understood that this processing may move to the mobile device to the extent the mobile device can support it, or another computing device.

As illustrated diagrammatically in FIG. 1, components of PU 50 may include:
(1) a database or library or the like 60 for generating or providing training programs to a user;
(2) sorting and processing procedures 70 to assess functional state and performed workload, and to make adjustments to prospective training programs (TPs); and
(3) various look up tables or the like 80 used in carrying out the functions of assessment and training program adjustment. These are discussed in more detail below.

The SATU 10 may take many forms without departing from the present invention. In one embodiment, the unit includes a plurality of sensor electrodes 12 that are capable of measuring bio-signals such as cardiac, brain wave and/or electrical muscle signals. Such sensors are known in the art. These sensors are connected to a transmitter or transceiver 15 that is capable of transmitting the sensed signals to the MD 20. The SATU to MD connection it is preferably wireless, though it may be wired. A suitable wireless SATU is taught by in co-pending U.S. patent application Ser. No. 13/912,176, referenced above, with sensors 41-46 and transmitter pod 50. Note, alternatively, that the SATU may be wired and the wiring may connect directly to a port on the mobile device, with appropriate channel amplifiers, filters, converters built into the wired connection and/or the MD. In this latter instance, the pod 50 of the co-pending application may not be needed. Furthermore, wireless sensors (ie, sensors with built in transmitters) may be used and may communicate directly to MD 20.

MD 20 is any suitable MD, and may take the form of a mobile phone, tablet computer, Blackberry®, or other mobile electronic communications device that may be carried with or otherwise borne by a user. MD 20 and/or SATU 10 may include GPS (standard on most cell phones), accelerometers, gyroscope, altimeter and/or other sensing or positioning technology, e.g., thermometer, wind-direction/speed detector, humidity meter, etc., for real time data collection. These positioning, environmental and other parameter measuring sensors may be represented generally with reference numeral 14.

The SATU 10 may also include an adjustable belt 13 that can be worn around a user's chest or elsewhere, and the transceiver/transmitter 15 that can be attached to the belt (or otherwise supported by the user). The GPS, accelerometer, gyroscope, altimeter, thermometer and/or other sensing/positioning technology 14 may be provided in or with (i.e., connected to) the transmitter 15 (if not otherwise provided on the user or in the mobile device, etc.). Placement of these sensors on the user (for example, with transmitter 15) gives an accurate measure of a user's movement for workload calculation.

The adaptive system of the present invention functions, in one embodiment, by establishing a base training program, assessing the current functional state of a user, assessing the workload performed by a user, and appropriately modifying the training program based on the assessed functional state and/or the workload measurements to provide a more optimum and effective overall training experience.

Figure 2:
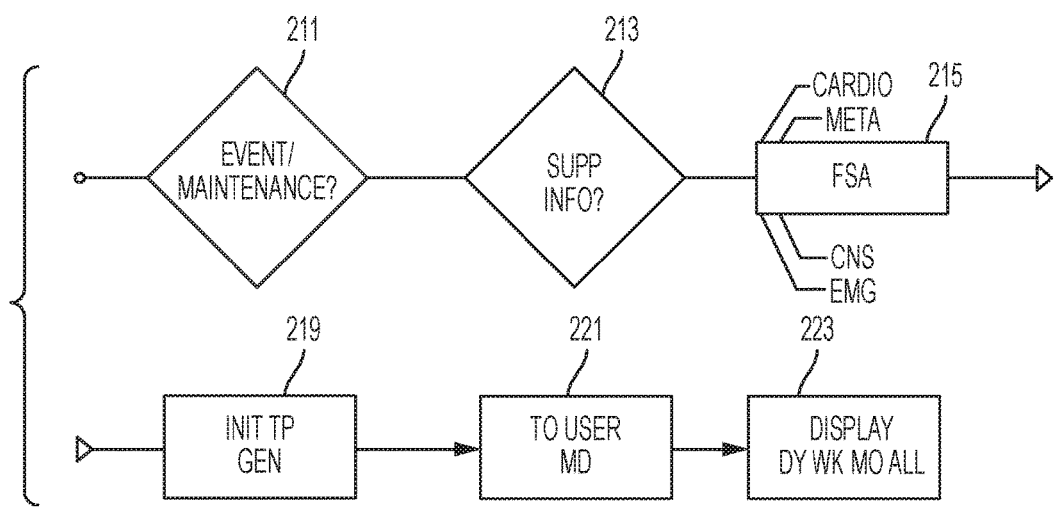
FIG. 2 is a block diagram illustrating one embodiment of initial training program generation in the system of FIG. 1.

Referring to FIG. 2, a block diagram illustrating one embodiment of initial training program generation is shown. A user, via user interface 20, is prompted for his or her training parameters (211).

Questions may include:
Are you training for an Event or Maintenance? If training for an Event, they may continue:
What is the Distance?
When is Event?
What is your desired Pace?

If the user indicates Maintenance rather than a Event, a similar list of questions is generated to determine the desired training program parameters. These questions might include historic run training, current physical state self-assessment, maintenance performance goals, etc.

For purposes of illustration, the assumed answers to the above questions (asked via step 211) are: Event, Marathon, 6 months, and 3H20 pace, respectively. In step 213, other information such as age, gender, height/weight, injury information, physical state self-assessment (e.g., self-stated fitness level), medical conditions, etc., may be elicited from a user. From this information, a base training program may be provided from training program library 60 (as discussed herein).

In one embodiment of the present invention, when the user is ready to begin their first training session, an initial functional state assessment (FSA) is conducted to determine the current physical state of the user. This information is used to create the initial training session target (as discussed below). The FSA may be conducted at rest and does not require the user to perform an initial load, e.g., run five miles. The present invention is unique in being able to assess functional state (readiness for exercise) without an initial load performance, and using the assessment result to more accurately craft an initial TP.

Various body system tests may be investigated during an FSA including cardiac, metabolic, central nervous system (CNS), hormonal, and electromyography (EMG), among others. These body system tests provide a picture of the current functional state of the user (and readiness for work). For example, the metabolic assessment (preferably derived from a differentiated ECG type signal) may give an indication of anaerobic threshold, important for use in generating an initial target heart rate (discussed in part below under Anaerobic Threshold). Heart Rate Variability (among other body system assessments) may be used to determine sympathetic and parasympathetic nervous system states, which are important in generating distance and intensity targets, etc.

The FSA of step 215 may include a differentiated ECG assessment to identify and/or closely approximate the Anaerobic Threshold (AT) of a user, and the target heart rate, BPM, that corresponds with that AT.

PU 50 may default to a conventional training program for the initial distance to be run (in generating a prospective TP).

PU 50 may further modify the prospective TP based on FSA data to arrive at an initial TP "session target" that is customized to the user (step 219). This will preferably be expressed in distance and heart rate targets. Step 221 represents propagation of the TP and session target to a user.

The TP and session targets may be viewed on MD 20 by Day, Week, Month, ALL or other (step 223), though what is particularly relevant is the target for the current day as future targets will likely change based on future FSA results and workload measurements (WLMs). Display of tentative future training targets may be helpful to a user in the general scheduling of their day-to-day affairs. Interface logic 20 may be configured with the MD software so that the training program is integrated into the calendar and alarm functions of the user's mobile device, so that a user may schedule their workout time in advance and be alerted by their MD. Food intake needs that support the proscribed physical activity may also be sent to MD 20 for display and integration into the MD's scheduling system, to assist a user in timely and appropriate food selections.

Use in Training

Figure 3:
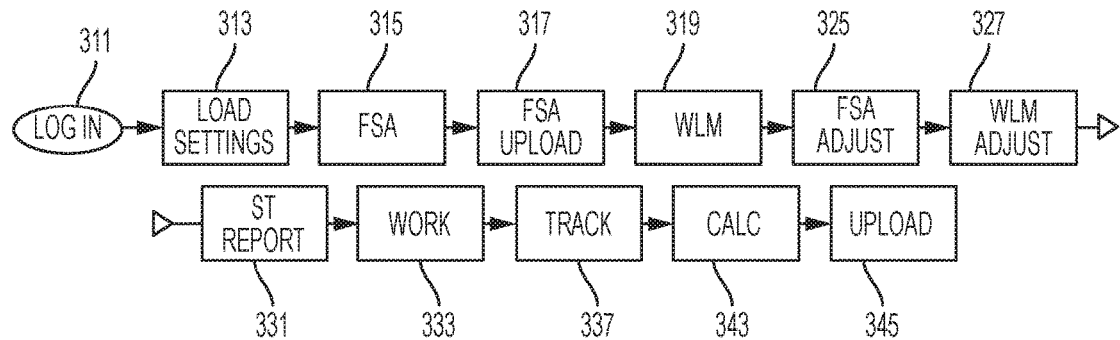
FIG. 3 is a flow diagram illustrating daily (or other period) use of the system of FIG. 1.

Referring to FIG. 3, a flow diagram illustrating daily (or other period) use of training system 5 is shown. This example could be for day 21, 57, 132 or any other given day, though if for day 1, there would be no workload history.

The user preferably logs in, step 311. Processing unit 50 loads the user's settings including the prospective Session Target (ST) for that day, step 313. The user is prompted for conducting a pre-load FSA, step 315. This prompting may include prompts for correct sensor placement and then sequentially stepping the user through the appropriate FSA test steps. In step 317, the results data is sent to PU 50. In step 319, PU 50 retrieves or uploads the most recent WLMs (performance history of the user). The FSA results and the WLMs of steps 317 and 319, respectively, are used to modify the prospective Session Target. The criteria for and manner of making ST adjustments are discussed in more detail below with reference to FIGS. 4 and 5.

In step 325, the prospective TP is modified, if necessary, based on the FSA results. In step 327, the FSA-adjusted prospective TP is modified, if necessary, based on WLMs.

In step 331, the target training program for the current session is presented to the user. In step 333, the "work" begins. This Start may be initiated by a user pushing Start on the user-interface or the sensors sensing movement of the user and initiating tracking, etc.

The workload parameters are preferably tracked in real-time, step 337. During the proscribed run, the user may be alerted if they vary from a proscribed BPM, pace, smoothness or other parameter. At completion of the work, the user may press an END button, or the sensors may END based on detected stopping (for longer than a traffic light, etc.), step 339. The user may be prompted for confirmation. Workload measurement calculations are preferably performed, step 343, and the WLMs uploaded to PU 50, step 345, so they are available during step 319 above as the preceding day's WLM.

Anaerobic Threshold

The metabolic assessment of the FSA is used to determine AT which in turn is used to generate an initial target heart rate (to maximize aerobic performance). Metabolic assessment is taught in U.S. Pat. No. 6,572,558 referenced above and Publications of Kiev Sports Medicine University by Beregovog, V.Y., or Dushanin, S.A. (1986).

Anaerobic exercise is exercise intense enough to trigger lactic acid fermentation. It is used by athletes in non-endurance sports to promote strength, speed and power and by body builders to build muscle mass. Muscle energy systems trained using anaerobic exercise develop differently compared to aerobic exercise, leading to greater performance in short duration, high intensity activities, which last from mere seconds to up to about 2 minutes. Any activity lasting longer than about two minutes has a large aerobic metabolic component.

The anaerobic threshold, also known as the lactate threshold, is the exercise intensity at which lactate (more specifically, lactic acid) starts to accumulate in the blood stream. This happens when lactate is produced faster than it can be metabolized in the muscle. When exercising at or below the AT, any lactate produced by the muscles is removed by the body without it building up. With a higher exercise intensity the lactate level in the blood reaches the AT, or the onset of blood lactate accumulation. The AT is a useful measure for deciding exercise intensity for training and racing, particularly in endurance sports (e.g. long distance running, cycling, rowing, swimming and cross country skiing), but varies between individuals and can be increased with training.

Influence of FSA and WLM

Figure 4:
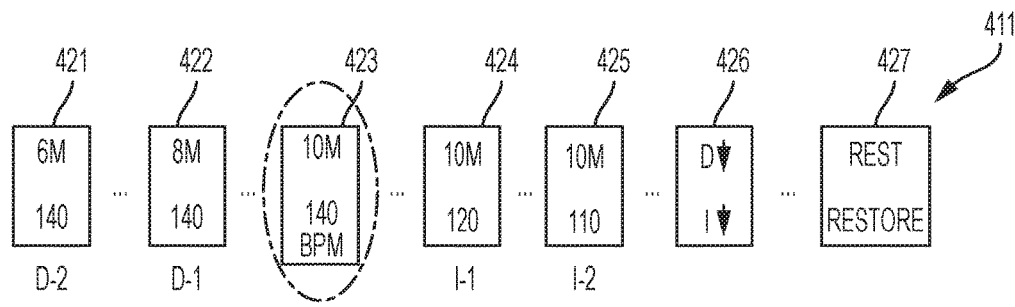
FIG. 4 is a spectrum of potential Day Targets.

Referring to FIG. 4, a spectrum 411 of potential session targets for a given training session is represented. Often there will be one training session per day, yet depending on the training program there may be multiple sessions in a day. Thus, the training targets may be referred to as session targets or STs. While only one ST is likely shown to a user, PU 50 may be configured to create session targets along a spectrum of different intensity and volume specifications. In the example of FIG. 4, ST 423 is a "prospective" or pre-FSA ST. The actual ST presented to the user, however, may shift to the left or to the right along the spectrum. Note that intensity and volume parameters may differ based on the type of athletic event. For distance running, the intensity parameter is preferably heart rate or BPM and the volume parameter is preferably distance. In other athletic pursuits, intensity might include number of repetitions or repetitions in a certain time period, and volume might include weight lifted or height climbed, etc.

In step 325 of FIG. 3, PU 50 investigates the results of the FSA of step 315. If all the relevant body systems are in sufficiently good condition, then target 423 is presented to the user. If, however, the results of the FSA suggest that one or more body systems are not optimal then another ST is presented. The "other" ST may have a reduced workload requirement and the type and magnitude of the reduction will depend on the FSA results.

In target 422, the "intensity" or BPM is maintained, yet the miles are reduced. In target 421, the miles are reduced even further, while intensity is unchanged. In target 424, conversely, the distance is maintained, but the intensity is reduced (slower run) and in ST 425, the intensity is reduced even further. ST 426 indicates a reduction in both distance and intensity, i.e., the user has a rather reduced state of readiness. ST 427 indicates rest or restorative therapies, i.e., the user is rather depleted. The intensity and distance proscriptions are influenced by the sympathetic and parasympathetic nervous systems, and other body systems.

Sympathetic/Parasympathetic Nervous Systems

The sympathetic and parasympathetic nervous systems (SNS, PSNS) are the two main divisions of the autonomic nervous system (ANS). The ANS is responsible for regulation of internal organs and glands, which occurs unconsciously. To be specific, the sympathetic nervous system is responsible for stimulation of activities associated with the fight-or-flight response. The parasympathetic system is responsible for stimulation of "rest-and-digest" activities that occur when the body is at rest, especially after eating, including sexual arousal, salivation, lacrimation (tears), urination, and digestion. Sympathetic and parasympathetic divisions typically function in opposition to each other, though in a complementary rather than antagonistic manner. The sympathetic division typically functions in actions requiring quick responses. The parasympathetic division functions with actions that do not require immediate response.

It is known in the art that heart rate variability evaluation may be used to assess the state of the SNS and PSNS. Good SNS levels indicate a person's ability to run a long distance, but do not well address intensity. Good PSNS levels indicate a person's ability to perform at higher intensity, but do not well address endurance and the ability to run long. Hence, when PSNS levels are high, but SNS levels are low, the ST shifts to the left and ST 422 or 421 is selected, based on the relative magnitude of PSNS and SNS levels. If the converse is found, the selected ST shifts to the right to the appropriate one of ST 424 and 425 (assuming other body system results are satisfactory).

If both SNS and PSNS are not within a sufficiently adequate range or another body system is low in combination with a low SNS or PSNS, then ST 426 may be selected. There may be a reduction to 8 miles at 120 BPM or 6 miles at 110 BPM, or other values or combinations, depending on the gravity of the FSA values. Further, a very strong negative FSA value in one body system parameter or an accumulation of lower FSA values (across multiple body systems) may indicate the need for rest—a day off—or, if lower yet, restorative activities such as massage, acupuncture, etc.

In addition to metabolic (DECG, AT, BPM) and cardiac (HRV, SNS/PSNS, Intensity/Distance), other body systems measurements may influence session target selection/creation. These include: DC Potential, Hormonal, Detoxification, Gas Exchange/Pulmonary and EMG, among others. The first four of these may be achieved using an omega brain wave test as described in the '558 patent, and the EMG test may be achieved using an EMG test as described in the co-pending application Ser. No. 13/912,176.

In essence, each of these tests has a normal range of results and the range can vary from person to person. The results for all of these tests are characterized in having an excitation component and an inhibition component. Thus, each test result may have an excitement result of: too excited, norm or not excited enough and an inhibition result of: too inhibited, norm, not inhibited enough. The adjustment to the training program will be to bring the user back towards a "norm" for each body system.

For example, if the CNS test (omega wave-DC potential) returns a low level, then this infers that the CNS is inhibited. High mental work or power exercise is not recommended. If the hormonal system is below a norm, then maximum velocity is not recommended. If the HR test returns a state of over excitement, then a reduced vigor workout is proscribed, to bring the excitement level back towards the norm.

For each body system assessment and correction, the path is rather linear—over/under and amount. The aggregate of the corrections/adjustments may be non-linear, however, due to the multiple body system factors influencing the adjustments.

Figure 5:
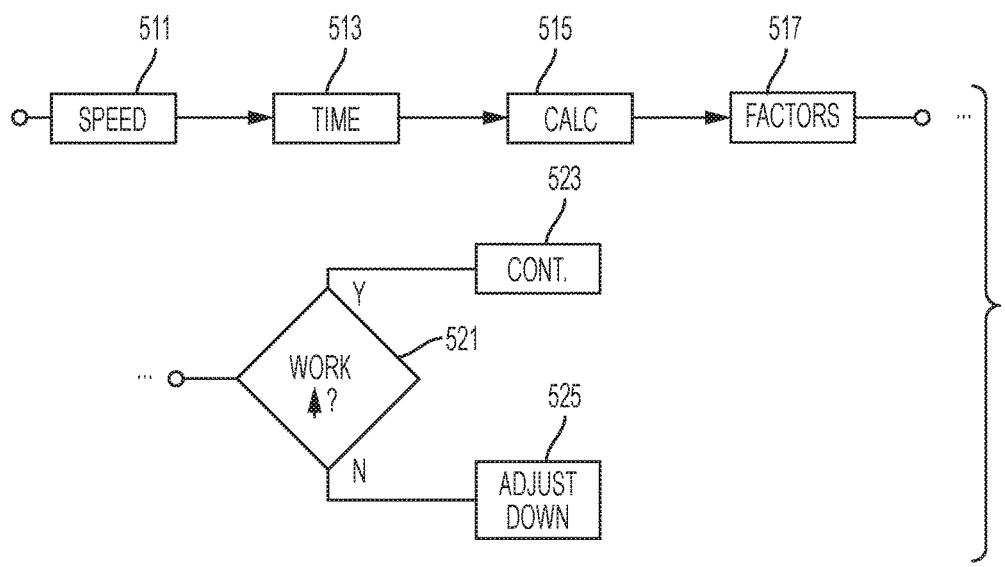
FIG. 5 is a flow diagram of computer workload measurement calculation and its influence on Day Target generation.

Referring to FIG. 5, a flow diagram of computer workload measurement calculation and its influence on ST generation is shown.

Step 327 of FIG. 3 represents adjustment of the TP based on WLM. For running, a desired goal is to increase speed and/or distance at speed. Thus, while the FSA tracks the functional state of the body at a given moment, it does not detect performance. The detection of performance provides feedback on whether the proscribed TP is actually working and providing the desired results.

A primary measure of workload is distance and speed. Assuming the same or approximately same training conditions (elevation, wind speed, etc.), then, week by week, for example, improvements in performance should be detected. If the performance is not improving (speed decreasing, targets not being met or increasingly missed, etc.), then the body is likely being driven too hard. To address this, the spectrum of day targets is preferably shifted down, which may be achieved primarily through reducing intensity, BPM. Mileage may be dropped though preferably merely to let the body recover and is then increased so that requisite mileage is achieved.

Furthermore, the WLM may be fine tuned by accounting for other factors such as elevation, windspeed, traffic light stoppage and other factors. An appropriate mathematical value can be assigned to one or more of these factors (and relative magnitude accounted for) and incorporated into the workload measurement calculation.

Thus, a first part of FIG. 5 represents determination of WLM (that generated in step 343 of FIG. 3). The distance (GPS) and time (clock) of the run is measured and a speed calculated, step 511, 513, 515. In step 517, the speed value may be adjusted for any of the condition factorials, etc.

The lower part of FIG. 5, step 521, illustrates comparison of the WLM (using the comparative processing 70 of PU 50), which may occur on a daily (or other) basis, yet for a period extending back one to several weeks (or more. If the performance is improving, no change in made to the TP, step 523. If, however, performance is not improving then the Session Targets are adjusted, preferably as discussed above (potentially shifted down), step 525.

It should be recognized that in addition to proscribing miles, intensity and other physical acts, the PU 50, through its database and processing ability, may also provide a user with nutritional information proscriptions to support the physical activity in the STs. This nutritional information may include the type of food to eat (protein, vitamin-rich, carbohydrate-rich, etc.), serving size, caloric intake, and other information, on a day-to-day (or other period) basis.

The above example is for marathon training. It should be further recognized that the present invention applies to other activities including longer and shorter distance running, sprinting, swimming, cross-country skiing, and cycling activities, etc. While well-suited for aerobic activities, it may also be used for anaerobic conditioning, i.e., providing repetitions and weight/resistance, and weight-lifting, etc.

U.S. Pat. No. 6,572,558 to Masakov et al, is incorporated by reference. This patent teaches that an HRV test or assessment may record bio-signal data, construct charts or "grams" that reflect the sensed data, calculate indices, and perform rules based analysis of the indices values to generate conclusions of the functional state of cardiac activity. Various indices for cardio system performance are calculated and they may include: vagus (parasympathetic) regulation (VR), humoral regulation (HR), sympathetic regulation (SR), stress index, share of aperiodic influences, standard deviation, and frequency of cardiac contractions.

With respect to DECG assessment, various DECG tests may be utilized without departing from the present invention. Bio-signal data is preferably recorded from the sensor electrodes for a predefined time period. Indices are then generated from the sensed data and the indices may include anaerobic power index (API) which is the magnitude of maximum oxygen consumption, VO2max, the alactic capacity index (ALCI), the lactic capacity index (LCI), the anaerobic capacity index (ACI), the aerobic efficiency index (AEI) and the system adaption index (SAI).

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

The invention claimed is:

1. A method for a portable electronic device to interact with at least one user borne sensor electrode to combine sensed data with user input goal data to generate a training session target, comprising the steps of:
   detecting, by the portable electronic device, input specifying user goal data, the goal data including a type of activity for the user, and storing the goal data in memory;
   detecting, by the portable electronic device, bio-signal data sensed from at least one sensor electrode that is positioned at an appropriate location on the user, for a heart rate variability (HRV) assessment of a current functional state of the user, and storing the detected HRV bio-signal data in memory;
   processing, by the portable electronic device or another device in communication with the portable electronic device, an HRV assessment of the detected HRV bio-signal data to generate a first index parameter indicative of the state of a first body system of the user that corresponds to the HRV assessment, and storing the first index parameter in memory;
   generating, by the portable electronic device or another device in communication with the portable electronic device, a session target for a given user training session that is based on retrieved user goal data and the first index parameter, the session target including a first session target value and a second session target value; and
   generating, by the portable electronic device, and displaying on a screen thereof, a visual indication of the first and the second session target values;
   wherein the first body system is the autonomic nervous system and the first and second session target values are based, at least in part, on the relative levels of the sympathetic nervous system and the parasympathetic nervous system of that user;
   wherein the first session target value is an intensity target and the second session target value is a volume target; and
   wherein the session target generating step further includes decreasing the volume target more than the intensity target when the parasympathetic level is high relative to the sympathetic level and decreasing the intensity target more than the volume target when the sympathetic level is high relative to the parasympathetic level.

2. The method of claim 1, further comprising the steps of:
   detecting, by the portable electronic device, sensed bio-signal data for an electrocardiogram (ECG) assessment of the current functional state of that user, and storing the detected ECG bio-signal data in memory;
   processing, by the portable electronic device or another device in communication with the portable electronic device, an ECG assessment of the ECG bio-signal data to generate a second index parameter indicative of the state of a second body system that corresponds to the ECG assessment, and storing the second index parameter in memory;
   adjusting, by the portable electronic device or another device in communication with the portable electronic device, the session target based on the second index parameter such that the first and second session target values are derived from the HRV and the ECG assessments and the user goal data.

3. The method of claim 1, further comprising the step of conducting the HRV assessment while the user is at rest.

4. The method of claim 1, further comprising the step of generating a training program based, at least in part, on user goal data, the training program including a plurality of session targets to be performed sequentially over time.

5. The method of claim 1, further comprising the steps of:
   detecting, by the portable electronic device, sensed bio-signal data for a brain wave assessment of the current functional state of that user, and storing the brain wave bio-signal data in memory;
   processing, by the portable electronic device or another device in communication with the portable electronic device, a brain wave assessment of the brain wave bio-signal data to generate a third parameter indicative of the state of a third body system that corresponds to the brain wave assessment, and storing the third parameter in memory;
   adjusting, by the portable electronic device or another device in communication with the portable electronic device, the session target based on the third index parameter such that the first and second session target values are derived from the HRV and the brain wave assessments and the user goal data.

6. The method of claim 1, wherein the session target generating step further comprises the step of generating a training program with a prospective session target and modifying the prospective session target based on the HRV assessment to generate the session target.

7. The method of claim 1, further comprising the steps of:
   establishing a training program for a given user, the training program including at least one session target that includes the first session value and the second session value.

8. The method of claim 2, wherein the first session target value includes an intensity target that is based on an anaerobic threshold as determined in the ECG assessment.

9. The method of claim 1, further comprising the steps of:
   detecting, by the portable electronic device, sensed bio-signal data for electromyography (EMG) assessment of the current functional state of that user, and storing the detected EMG bio-signal data in memory;
   processing, by the portable electronic device or another device in communication with the portable electronic device, an EMG assessment of the EMG bio-signal data to generate a third parameter indicative of the state of a third body system that corresponds to the EMG assessment, and storing the third parameter in memory;
   adjusting, by the portable electronic device or another device in communication with the portable electronic device, the session target based on the third parameter such that the first and second session target values are derived, at least in part, from the HRV and the EMG assessments and the user goal data.

10. A method for a portable electronic device to interact with at least one user borne sensor electrode to combine sensed data with user input goal data to generate a training session target, comprising the steps of:

detecting, by the portable electronic device, input specifying user goal data, the goal data including a type of activity for the user, and storing the goal data in memory;

generating, by the portable electronic device or another device in communication with the portable electronic device, a prospective training program for the user based on the input goal data, the training program including a plurality of prospective session targets to be performed sequentially over time;

detecting, by the portable electronic device, bio-signal data sensed by at least one sensor electrode that is positioned at an appropriate location on the user, for a heart rate variability (HRV) assessment of a current functional state of the user, and storing the detected HRV bio-signal data in memory;

processing, by the portable electronic device or another device in communication with the portable electronic device, an HRV assessment of the detected HRV bio-signal data to generate a first index parameter indicative of the state of a first body system that corresponds to the HRV assessment, and storing the first index parameter in memory;

modifying, by the portable electronic device or another device in communication with the portable electronic device, the prospective training program to generate a session target for a given user training session that is based on the first index parameter, the session target including a first session target value and a second session target value; and generating, by the portable electronic device, and displaying on a screen thereof, a visual indication of the first and the second session target values;

wherein the first body system is an autonomic nervous system and the first and second session target values are based, at least in part, on the relative levels of the sympathetic nervous system and the parasympathetic nervous system of the user;

wherein the first session target value is an intensity target and the second session target value is a volume target; and wherein the session target generating step further includes decreasing the volume target more than the intensity target when the parasympathetic level is high relative to the sympathetic level and decreasing the intensity target more than the volume target when the sympathetic level is high relative to the parasympathetic level.

11. The method of claim 10, further comprising the step of detecting the bio-signal data from the user while the user is at rest.

12. The method of claim 11, further comprising the step of:

detecting, by the portable electronic device and for a defined period of time, sensed bio-signal data for electrocardiogram (ECG) assessment of the current functional state of that user, and storing the detected ECG bio-signal data in memory;

processing, by the portable electronic device or another device in communication with the portable electronic device, an ECG assessment of the ECG bio-signal data to generate a second index parameter indicative of the state of a second body system that corresponds to the ECG assessment, and storing the second index parameter in memory; and modifying, by the portable electronic device or another device in communication with the portable electronic device, the prospective training program based on the second index parameter such that the session target is generated from the HRV and the ECG assessments and the user goal data;

wherein the session target is derived in part from an anaerobic threshold of the user as determined by the ECG assessment.

* * * * *